US00PP07879P

United States Patent [19]

Fruehwirth

[11] Patent Number: Plant 7,879

[45] Date of Patent: Jun. 2, 1992

[54] POINSETTIA PLANT '441'

[75] Inventor: Franz Fruehwirth, Encinitas, Calif.

[73] Assignee: Paul Ecke Ranch, Inc., Encinitas, Calif.

[21] Appl. No.: 528,238

[22] Filed: May 24, 1990

[51] Int. Cl.[5] ..... A01H 5/00

[52] U.S. Cl. ..... Plt./86

[58] Field of Search ..... Plt./86, 86.4

[56] References Cited

U.S. PATENT DOCUMENTS

| | | | |
|---|---|---|---|
| P.P. 4,235 | 4/1978 | Gutbier | Plt. 86 |
| P.P. 6,694 | 3/1989 | Ecke, Jr. | Plt. 86 |
| 4,724,276 | 2/1988 | Ecke, Jr. | 47/58 |

*Primary Examiner*—Howard J. Locker
*Attorney, Agent, or Firm*—Arnold, White & Durkee

[57] ABSTRACT

Poinsettia '441' is a stiff-stemmed, early flowering cultivar with dark red flower bracts. It has dark green, medium size foliage and a strong branching habit. The plant height is medium and some chemical growth retardants may be needed to control the height of flowering plants. The appearance and cultural requirements are very similar to Poinsettia 'Lilo' (U.S. Plant Pat. No. 6,694). However, stronger self-branching traits and better post-production keeping qualities make '441' a more desirable commercial cultivar than 'Lilo'.

1 Drawing Sheet

BACKGROUND OF THE NEW PLANT

Poinsettia cultivar '441' is an induced mutant of a Poinsettia seedling designated 'E-60'. The new cultivar is similar to 'E-60' in having stiff, erect stems. However, cultivar '441' is strongly self-branching while the parent plant 'E-60' is notably less self-branching. Cultivar '441's post-harvest qualities are superior to those of 'Lilo' described in U.S. Plant Pat. No. 6,694.

This new Poinsettia cultivar '441' originated as an induced mutation of a seedling designated as 'E-60' which resulted from cross pollination in my greenhouse in Encinitas, Calif. It was selected because of its early flowering, medium stature, dark red flower bracts and dark green foliage, prolific branching and long post-production keeping; traits which distinguish it from other Poinsettia cultivars and seem to make it a desirable plant for commercial greenhouse production. '441' has many of the same desirable traits and appearances as Poinsettia 'Lilo'. However, greenhouse observations and post-production trials indicated stronger self-branching and almost no post-production bract edge burn. These characteristics are highly desirable in a commercially grown cultivar, and represent improvements over the cultivar 'Lilo'. After selection, stem cuttings of this plant were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia '441' is illustrated in the accompanying color photographs.

The upper photo is a side view of 3 single stem plants per pot in full flower. Evidence of strong self-branching traits can be observed by the numerous flowering axillary branches on these unpinched plants.

The lower photo is a top view of the same plant showing flower and bract formation.

DESCRIPTION OF THE PLANT

The following is a detailed description of this new poinsettia as observed in my greenhouse in Encinitas, Calif., during December 1989. Observations were recorded from flowering plants, grown as 3 unpinched plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of a 'E-60'; this sport was induced by application of the procedures set forth in U.S. Pat. No. 4,724,276 to the seedling parent.

Classification:

*Botanic.*—*Euphorbia pulcherrima* Willd.

*Common name.*—Poinsettia.

*Cultivar name.*—'441'.

Form: Shrub.

Height: Medium.

Growth habit: As a single stemmed plant, upright and medium height. This height is typically taller than 'Gutbier V-10', which under the same growing conditions may attain an overall height of 35–36 cm (short), while a pot of '441' would have a height of 42 cm (medium). The stems are stiff and self supporting, in contrast with 'V-10' which may not be self-supporting if growing conditions are too warm or the growing medium is soft. The application of a chemical growth retardant may be needed to restrict height for commercial pot plant production. I observed 3 plants in a pot with an overall height of 42 cm. and an overall width of 45 cm. The bract diameter of individual flowers was 32 cm.

Branching: Poinsettia '441' has strong self-branching traits. Axillary branches will develop and terminate in a flower without pinching. More of these axillary branches develop on '441' than on similar cultivar 'Lilo'. It may be desirable to pinch '441' and remove all terminal dominance. then 6–8 axillary branches may develop uniformly and at a faster rate. In contrast, pinching of 'Lilo' results in 5 branches.

Growth rate: Rooting of stem cuttings occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The color is much darker than RHS 139A. On the other hand, the leaf color of 'Gutbier V-10' while darker than foliage on other cultivars and similar in tone to '441', is distinctly lighter than RHS 139A, the darkest green color available in the RHS series color charts. The leaves are of medium size, leaf blades typically being about 12–14 cm. long and about 9–10 cm. wide with leaf petioles about 6 cm. long.

Leaf

*Shape.*—Typical leaves are ovate with obtuse bases and acuminate tips. Leaf margins are entire or somewhat lobed with 1 or 2 indentations on each side of the leaf blade.

*Color.*—Upper side — Dark green, darker than RHS 139A. Underside — Green, between RHS 147A and RHS 147B.

*Retention.*—The foliage lasts extremely well under low light intensities in the consumer's home. '441' has superior leaf retention, equal to or better than 'Lilo' or 'V-10'.

Bracts: Generally there are 18–24 uniformly colored bracts of various sizes subtending the cyathia. The primary bracts have blades typically 14–16 cm. long and 8–10 cm. wide with petioles about 5 cm. long.

*Shape.*—Bracts are mostly ovate to elliptic with acute bases and acuminate tips. Primary bracts are slightly lobed with 1 or 2 indentations on either side of the bract. Secondary bracts have entire margins.

*Color.—Upper side — Dark red, darker than RHS* 46B, near RHS 46A. Underside — Red, darker than RHS 45D near RHS 45C. By comparison, the bract color of 'Gutbier V-10' is a bright red, between RHS 46A, 46B and 45A on the upperside and near RHS 45B on the underside.

*Retention.*—Bract retention is strong, even under low light intensities in consumer's homes. '441' also exhibits strong resistance to drying or "burning" of bract margins, and is superior to 'Lilo' in this respect.

Flowers: Generally, 15–21 cyathia (flowers) are present when the plant is in full bloom. Each cyathium is about 7–8 mm long and about 5 mm wide, green in color and fringed with red at the distal end. A single yellow nectar cup protrudes from the side of each cyathium. The flower pedicel is green and about 7–8 mm in length. The stamens protruding from the cyathia are red.

What is claimed is:

1. A new and distinct Poinsettia cultivar, substantially as herein shown and described, characterized by its early flowering, medium stature, dark red flower bracts and dark green foliage, and prolific branching.

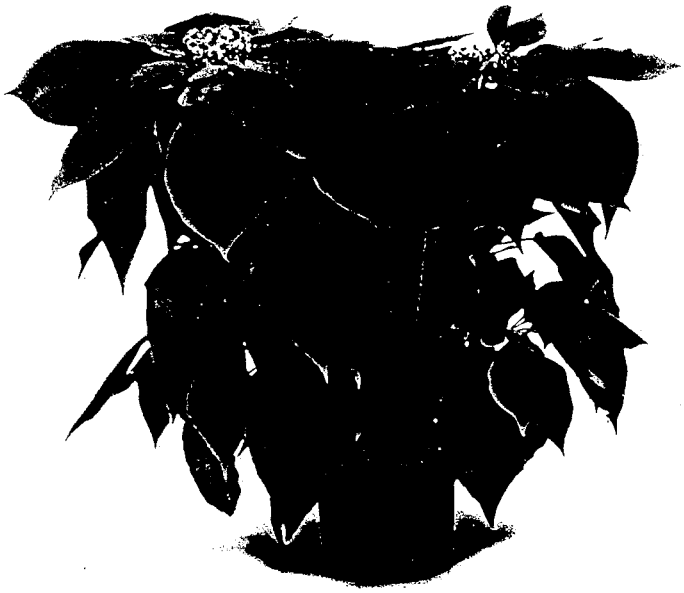
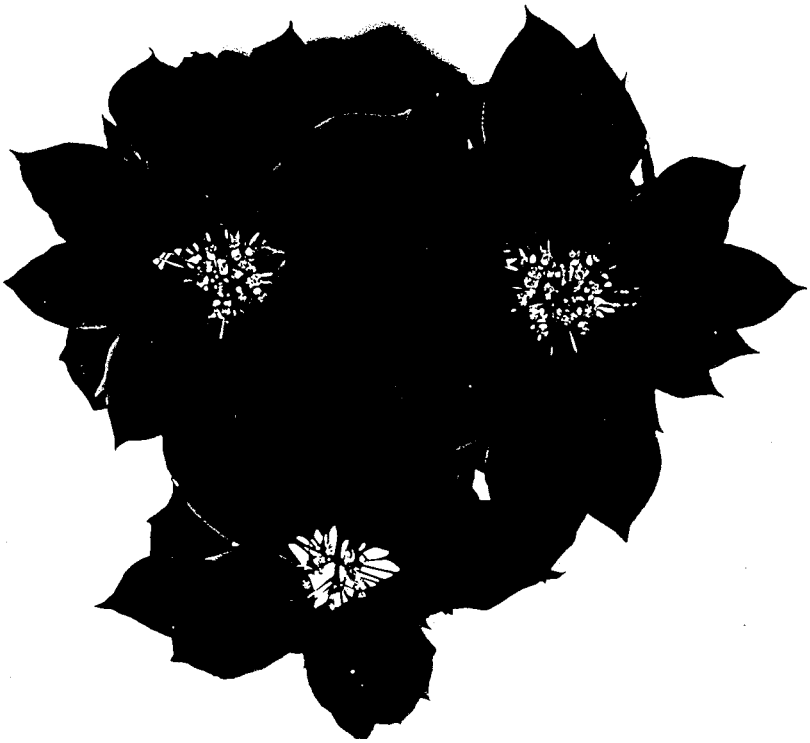

* * * * *